(12) United States Patent
Shembel et al.

(10) Patent No.: US 6,858,346 B2
(45) Date of Patent: Feb. 22, 2005

(54) SALTS OF ALKALI METALS OF N, N' DISUBSTITUTED AMIDES OF ALKANE SULFINIC ACID AND NONAQUEOUS ELECTROLYTES ON THEIR BASIS

(75) Inventors: Elena Shembel, Dnepropetrovsk (UA); Ivan V. Koval, Dniepropetrovsk (UA); Tat'yna G. Oliynik, Dnepropetrovsk (UA); Oleg V. Chervakov, Dnepropetrovsk (UA); Peter Novak, Antwerp (BE)

(73) Assignee: ENER1 Battery Company, Ft. Lauderdale, FL (US)

( * ) Notice: Subject to any disclaimer, the term of this patent is extended or adjusted under 35 U.S.C. 154(b) by 70 days.

(21) Appl. No.: 10/122,788

(22) Filed: Apr. 15, 2002

(65) Prior Publication Data

US 2003/0194612 A1 Oct. 16, 2003

(51) Int. Cl.$^7$ ................................................. H01M 6/04
(52) U.S. Cl. ........................ 429/188; 429/307; 429/314; 429/316; 429/317; 429/322; 429/323; 429/324; 429/338

(58) Field of Search .................................. 429/324, 338, 429/322, 323, 188, 307, 314, 316, 317

(56) References Cited

FOREIGN PATENT DOCUMENTS

SU        287932 A    *   2/1971

* cited by examiner

*Primary Examiner*—Laura Weiner
(74) *Attorney, Agent, or Firm*—Akerman Senterfitt (57) ABSTRACT

An organic salt having an alkali metal bound to a disubstituted amide of alkane iminosulfinic acid has the following general formula:

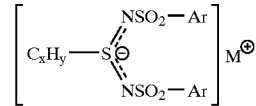

where Ar is an aromatic group, M is an alkali metal such as Li, K or Na, and $C_xH_y$ is an alkane. The organic salt can be used to form non-aqueous liquid and gel or plasticized polymer electrolytes. The electrolytes can be used to form improved lithium and lithium ion batteries.

32 Claims, 5 Drawing Sheets

SALTS OF ALKALI METALS OF N, N' DISUBSTITUTED AMIDES OF ALKANE SULFINIC ACID AND NONAQUEOUS ELECTROLYTES ON THEIR BASIS

CROSS-REFERENCE TO RELATED APPLICATIONS

Not applicable

STATEMENT REGARDING FEDERALLY SPONSORED RESEARCH OR DEVELOPMENT

Not applicable

FIELD OF THE INVENTION

The invention relates to nonaqueous electrolytes for electrochemical cells, and more particularly to organic alkali metal salts for such cells.

BACKGROUND OF THE INVENTION

The demand for new and improved electronic devices such as cellular phones, notebook computers and compact camcorders have demanded energy storage devices having increasingly higher specific energy densities. A number of advanced battery technologies have recently been developed to service these devices, such as metal hydride (e.g., Ni—MH) and lithium batteries with liquid electrolytes. More recently, lithium batteries with polymer electrolytes have been introduced.

Lithium batteries can be either lithium ion batteries or lithium metal batteries. Lithium ion batteries intercalate lithium ions in a host material, such as graphite, to form the anode. On the other hand, lithium metal batteries use metallic lithium for the anode.

The electrolyte used in lithium batteries can be a liquid or a polymer electrolyte. Lithium batteries having liquid electrolytes have been on the market for several years. Lithium batteries having polymer electrolytes are comparatively new entries into the marketplace.

Lithium batteries having polymer electrolytes represent an evolving alternative to lithium batteries having liquid electrolytes. The polymer electrolyte provides a medium for ionic conduction analogous to the liquid electrolyte in a Li battery having a liquid electrolyte. Typical polymer electrolytes include polyethylene oxide (PEO), polyacrylonitrile (PAN), polymethylmethacrylate (PMMA) and polyvinylidene fluoride (PVDF).

Because its electrolyte is a non-volatile material which cannot leak, a lithium battery having a polymer electrolyte is intrinsically safer that a lithium battery having a liquid electrolyte. Moreover, polymer electrolytes eliminate the need for venting and package pressure which are generally required for operation of lithium batteries having liquid electrolytes. Thus, polymer electrolytes make it possible to use a soft outer case such as a metal plastic laminate bag, resulting in improvement in weight and thickness, when compared to liquid electrolyte can-type Li batteries. In addition, recent research has indicated that electrode materials generally react less with polymer electrolytes compared to liquid electrolytes, even under abuse conditions. This should constitute a significant safety advantage for stable charging-discharging of Li batteries having polymer electrolytes over conventional Li batteries having liquid electrolytes. Lithium batteries having solid polymer electrolytes are also considered environmentally acceptable.

Lithium batteries having polymer electrolytes are generally configured as gel-type or plasticized polymer electrolytes which have liquid electrolytes intermixed with a selected polymer electrolyte matrix material. The liquid electrolyte generally includes a salt of an alkali metal and an aprotic solvent. The salt and the aprotic solvent comprising the liquid electrolyte are integrated with the polymer material to form the gel-type or plasticized polymer material.

The polymer electrolyte functions as a separator, being interposed between the cathode and anode films of the battery. Each cathode, separator and anode combination forms a unit battery cell. Practical lithium batteries, such as those having polymer electrolytes, are generally prepared by stacking a number of battery cells in series to achieve desired battery capacity.

Many performance parameters of lithium batteries are associated with the electrolyte choice, and the interaction of the selected electrolyte with the cathode and anode materials used. High electrolyte ionic conductivity generally results in improved battery performance. The ionic conductivity of polymer electrolytes has been reported to as high as approximately $10^{-4}$ S/cm. However, it is desirable for the ionic conductivity of the polymer electrolyte to reach a value of at least approximately $10^{-3}$ S/cm for many battery applications. In addition, it would also be desirable to enhance the electrochemical stability of the polymer electrolyte towards anode and cathode materials to improve battery reliability, as well as storage and cycling characteristics.

The ionic conductivity of a gel or plasticized polymer electrolyte can be significantly influenced by the specific alkali metal salt and aprotic solvent used. In polymer electrolytes, inorganic lithium salts, such as $LiClO_4$, $LiAsF_6$, $LiPF_6$ and $LiBF_4$, are widely used as traditional ion-conducting additives.

The lithium salt can influence the performance of rechargeable lithium-polymer power sources by affecting the transport of lithium ions in the volume of the polymer electrolyte and at the electrode/electrolyte interface or the formation of passivating layers at the electrode/polymer electrolyte interface, which are known to generally change during charge/discharge cycling.

In plasticized and gel-like polymer electrolytes containing as a plasticizer an aprotic solvent, cations and anions derived from lithium salts are each mobile. As a rule, the transport number of lithium ions in these systems is far less than 1 (usually ~0.5). Such a situation can result from cation binding by the polar groups of polymer matrix, such as —O— in polyethylene oxide, —CN in polyacrylonitrile and—NR in polyamide. Therefore, in certain electrolytes including lithium salts, the anion can contribute to the overall ionic conductivity more than the cation can.

The problems of undesirable participation of anions in ion transport and decreasing reactivity of polymer electrolytes relative to the electrode materials can be solved by using lithium organic salts with large anions. It is evidenced by the increased interest in lithium imide salts of the $LiN(SO_3CF_3)_2$, $[(CF_3SO_2)(C_4F_9SO_2)]NLi$, $(C_4F_9SO_2)_2NLi$, types [J. Kuratomi, T. Iguchi, T. Bando, Y. Aihara, T. Ono, K. Kuwana. Development of Solid-Polymer Lithium Secondary Batteries//$10^{th}$ International meeting on Lithium Batteries "Lithium 2000", Villa Erba Conference Center, Como, Italy, May 28–Jun. 2, Abstr.373] in the formation of polymer electrolytes.

Charge delocalization ability by the anion part of the salt resulting in their electrochemical and thermal stability is a characteristics property of these salts [J. Barthel, R.

Buestrich, H. J. Gores, M. Schmidt, M. Wehr, J.Electrochem.Soc, Vol. 144, N 11. 1997. P.3866–3870].

In the case of organic anions, these properties are known to depend directly on the acidity value of the corresponding organic acid. Salts which produce relatively strong NH-acid values can provide gel polymer electrolytes with high ionic conductivity. Some salts can also act as stabilizers with respect to thermo-oxidative destruction of polymers.

This is especially true for polymer electrolytes based on halogen-comprising polymers, for example, on the basis of polyvinylchloride (PVC) and its derivatives. Lithium salts like $LiClO_4$, $LiAsF_6$, $LiPF_6$, $LiBF_4$ are know to cause a thermal destruction of polymer electrolytes based on chlorinated polyvinyl chloride at above 50° C. [E. M. Shembel, O. V. Chervakov et al. Investigation of the stability of chlorinated PVC-based polymer electrolyte for lithium power sources//Journal Power Sources, 96 (2001) 20–28]. This limits the use of such polymer electrolytes in the composition of lithium power sources with operating temperature ranging from about –30 to +60° C.

SUMMARY OF THE INVENTION

A non-aqueous electrolyte includes an aprotic solvent and an organic salt. The organic salt is an alkali metal bound to a disubstituted amide of alkane iminosulfinic acid. The organic salt has the following general formula:

where Ar is an aromatic, M is at least one selected from the group consisting of Li, K and Na, and CxHy is an alkane, such as methane, ethane, propane, butane, pentane, hexane, heptane, octane and nonane. The alkali metal can be selected from Li, K or Na. One or both amides can be either benzene sulfonyl amide and para-toluene sulfonyl amide.

The aprotic solvent can be acrylonitrile, dimethyl formamide, dimethyl acetamide, dimethyl sulfoxide, propylene carbonate, ethylene carbonate, dimethyl carbonate, gamma-butyrolactone, 1,3-dioxolane, diglyme, dimethoxy ethane and sulfolane, and mixtures thereof.

The electrolyte can optionally include at least one inorganic salt. The inorganic salt can be $LiClO_4$, $LiBF_4$, $LiAsF_6$, $LiCF_3SO_3$ or $LiN(CF_3SO_2)_2$. Up to 10 weight percent of the electrolyte can be from the inorganic salt.

The electrolyte can include a polymer material. In this embodiment, the liquid electrolyte including the organic salt and aprotic solvent are preferably integrated with the polymer material to form a gel or plasticized polymer electrolyte. The polymer material can be polyethylene oxide, polyacrylonitrile, polymethylmethacrylate, a halogen-containing polymer, their copolymers, and mixtures thereof. The halogen-containing polymer can be polyvinyl chloride (PVC), chlorinated polyvinyl chloride, polyvinylidene fluoride, their copolymers and mixtures thereof. The polymeric material can comprise 10 to 85 weight percent of the polymer electrolyte. The aprotic solvent can be from 10 to 82 weight percent of the polymer electrolyte.

A method for forming an alkali disubstituted amide of alkane iminosulfinic acid salt includes the steps of providing disubstituted amides of alkane iminosulfinic acid, a source of alkali metal ions and at least one organic solvent, and mixing together the substituted alkane iminosulfinic acid, the source of alkali metal ions and the organic solvent. The method can include the step of evaporating the organic solvent. The source of alkali metal ions can include an alkali metal hydroxide or an alkali metal alcoholate. The amides can be benzene sulfonyl amide or para-toluene sulfonyl amide.

A method of forming a liquid electrolyte includes the steps of providing an aprotic solvent and an organic salt. The organic salt is an alkali metal bound to a disubstituted amide of alkane iminosulfinic acid. The aprotic solvent, inorganic salt and organic salt are then mixed together.

A method of forming a polymer electrolyte includes the steps of providing an aprotic solvent, a inorganic salt of an alkali metal, a polymer, and an organic salt. The organic salt comprises an alkali metal bound to a disubstituted amide of alkane iminosulfinic acid. The aprotic solvent, inorganic salt, polymer and organic salt are then mixed together. The polymer preferably comprises chlorinated PVC or PVDF.

A lithium battery includes a lithium or lithium ion containing anode, a cathode, and an electrolyte operatively associated with the anode and cathode. The electrolyte can be selected from the liquid electrolyte of claim 1 or the polymer electrolyte of claim 12. The battery can be rechargeable.

The anode can comprise lithium metal, such as a lithium metal alloy. The lithium alloy can be lithium-aluminum, lithium-aluminum-silicon, lithium-aluminum-cadmium, lithium-aluminum-bismuth or lithium-aluminum-tin.

The battery can be a lithium ion battery. In this embodiment, the anode comprises said lithium ions, such as a graphite based Li ion containing anode.

The cathode can include a metal oxide, such as a lithium-transition metal oxide. The metal oxide can be $MnO_2$, $LiMn_2O_4$, $V_2O_5$ or $V_6O_{13}$.

A method of forming an electrochemical cell includes the steps of providing an anode comprising an alkali metal or an alkali ion, a cathode, and a non aqueous electrolyte including an organic salt, the organic salt being an alkali metal bound to a disubstituted amide of alkane iminosulfinic acid. The electrolyte is then operatively associated with the anode and the cathode.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE PREFERRED EMBODIMENTS

The invention is related to organic salts of alkali metals and nonaqueous electrolytes formed from these salts for use in high energy primary and secondary batteries. The organic salt has an alkali metal bound to a disubstituted amide of alkane iminosulfinic acid.

The salts described herein are suitable for use in liquid electrolytes or polymer electrolytes, such as gel or plasticized polymer electrolytes. Although this detailed description will generally describe a gel and plasticized polymer electrolyte formed using salts from the invention, it should be understood that the organic salts desribed herein in combination with nonaqueous solvents are also useful for lithium batteries having liquid electrolytes.

In the case of a gel and plasticized polymer electrolyte, the nonaqueous gel or plasticized polymer electrolyte includes a polymer electrolyte material and a liquid electrolyte. The liquid electrolyte includes an organic salt as described above and a non-aqueous organic solvent, such as an aprotic solvent. The liquid electrolyte is integrated with the polymer matrix to form a modified polymer material which is generally referred to as a gel or plasticized polymer electrolyte. In a preferred embodiment of the invention, the salt is an alkali metal bonded to an N, N'-disubstituted amide of pentane iminosulfinic acid. Such salts have been previously unknown. The resulting nonaqueous electrolytes using the salts described herein provide high ionic conductivity as well as high levels of electrochemical and chemical stability for electrochemical cells formed using the invention. As a result, the invention can be used to produce batteries having improved properties.

A wide range of aprotic solvents may be used with the invention. For example, the solvent can be selected from dimethyl acetamide, propylene carbonate, ethylene carbonate, dimethyl carbonate, gamma-butyrolactone, 1,3-dioxolane, dimethoxy ethane, sulfolane, acrylonitrile, dimethyl sulfoxide or dimethyl formamide, and mixtures thereof.

Gel and plasticized polymer electrolyte characteristics generally depend on the nature of polymer matrix, the lithium salt, the nonaqueous solvent (e.g. aprotic solvent) and other optional electrolyte components (e.g. stabilizers) which may be added. In addition, the ratio of these components can also be determinative of the resulting electrolyte characteristics.

The concentration dependence of the specific electrical conductivity of salt solutions in aprotic solvents is known to reach a maximum value in the concentration range of approximately 1 M. However, in solvents with a dielectric constant $\in$ lower than approximately 30, the electric conductivity maximum generally shifts to higher salt concentrations, such as approximately 2.5 M. For example, dimethyl carbonate $\in=3.12$ and diethyl carbonate $\in=2.82$ both have dielectric constants $\in$ below 30. This shift in maximum electric conductivity to higher salt concentrations has been explained by a shift in ion equilibrium towards the formation of ion associates (ion pairs).

The ions Li, $ClO_4^-$, $BF_4^-$, $AsF_6^-$, $PF_6^-$ are known to decompose certain components of nonaqueous electrolytes during battery operation [U. Heider, R. Oesten, M. Jungnitz//J. Power Sources, 81–82 (1999)]. This electrolyte decomposition can lead to the formation of hydrofluoric acid or other acids which can cause further degradation of the electrolyte. Accordingly, when salts are used in rechargeable batteries, modifying additives such as tributylamine are generally added to the electrolyte solution to prevent or reduce electrolyte decomposition [D. Aurbach, E. Zinigrad, H. Teller, P. Dan, J. Electrochem. Soc., 147 (4) 1274–1279 (2000)].

When choosing an aprotic solvent, the stability of the nonaqueous electrolyte system over a wide potential range should generally be considered. Among known systems, the widest stability range is from approximately 4.5 to 5.0 V and is observed for lithium perchlorate salt in either acrylonitrile, dimethyl sulfoxide or dimethyl formamide solvents.

It is known [see I. V. Koval, Sulfurs Reports, 14, (1993) 149], that structural analogies of disubstituted amides of iminosulfinic acid (such as, N,N'-bis(arylsulfonyl)alkane sulfinyl amides) are more stable compounds in comparison with the derivatives of the chlorine and fluoride containing sulfinyl amides. They are stable in alkaline media and are hydrolyzed only when heated. The organic salts disclosed herein having alkali metal bound to a disubstituted amide of alkane iminosulfinic acid have also been found to be quite stable.

A method of preparing a nonaqueous electrolyte including a specie of a salt having an alkali metal bound to a disubstituted amide of alkane iminosulfinic acid may be prepared using a neutralization reaction. In the neutralization reaction, a disubstituted amide of an alkane iminosulfinic acid is reacted with an equivalent amount of alkali metal hydroxide or alkali metal ethylate.

The reaction is preferably performed in a suitable nonaqueous solvent, such as an acetone-ethanol solvent mixture. The substituted groups are preferably aromatic sulfur containing groups. More preferably, the substituted groups can be benzene sulfonyl ($C_6H_5SO_2$) or para-toluene sulfonyl ($CH_3C_6H_5SO_2$). A generalized neutralization reaction of a disubstituted amide of an alkane sulfinic acid is shown generally below:

where Ar is an aromatic group. As noted above, Ar is preferably benzene or toluene to form the substituted groups of benzene sulfonyl ($C_6H_5SO_2$) and para-toluene sulfonyl ($CH_3C_6H_5SO_2$), respectively. M is an alkali metal, such as Li, K or Na. The hydrocarbon $C_xH_y$ can be methane, ethane, butane, propane, pentane, hexane, heptane, octane, nonane or other alkanes. The hydrocarbon is preferably pentane. Thus, the disubstituted alkane iminosulfinic acid shown above can be disubstituted methane, ethane, butane, propane, pentane, hexane, heptane, octane, nonane or other alkanes of iminosulfonic acid.

The solvents can be evaporated in open air. The lithium salt product can then be dried in a suitable drying device, such as an exicator over $CaCl_2$ (nonaqueous) for about at least 7 days to remove moisture.

Liquid electrolytes suitable for use in batteries can be obtained by dissolving the synthesized solid salts in aprotic solvents, such as acrylonitrile, dimethyl sulfoxide, dimethyl formamide, dimethyl acetamide, propylene carbonate, ethylene carbonate, dimethyl carbonate, gamma-butyrolactone, 1,3-dioxolane, dimethoxy ethane, sulfolane and mixtures thereof. The concentration of the lithium salt in the electrolyte can range from approximately 0.01 to 10 M, preferably being between 0.1 M to 1.0 M.

The liquid electrolyte can then be used for the preparation of gel like or plasticized polymer electrolytes based on a variety of polymers such as polyethylene oxide (PEO), polyacrylonitrile (PAN), polymethylmethacrylate (PMMA), polyvinylidine fluoride (PVDF), polyvinylchloride (PVC).

A preferred modified polymer material for use with the invention is described in copending U.S. patent application Ser. No. 10/038,556 filed on Jan. 4, 2002 entitled SOLID POLYMER ELECTROLYTE LITHIUM BATTERY. In that application, a polymer electrolyte and methods for forming the same is described which includes a modified polymeric material. This copending application is assigned to the same assignee as the present application and is hereby incorporated by reference in its entirety in this application. The modified polymeric material includes a halogen containing polymer having an enhanced halogen level, the enhanced halogen level relative to a halogen content of the halogen containing polymer formed from polymerization of its monomer. The halogen containing polymer is preferably PVC obtained by emulsion or suspension polymerization of vinylchloride. In the case of chlorination of PVC, the resulting modified polymeric material preferably has 60–72 wt % chlorine as compared to the approximately 58.4 wt. % which results from the polymerization of the monomer ethylene chloride (vinyl chloride). As used herein, "chlorinated PVC" refers to a modified PVC polymer having 60–72 wt % chlorine.

Several of the many possible methods for making and using the invention may be illustrated by the following specific examples. The examples presented below are not intended to in any way limit the scope of the invention.

EXAMPLE 1
Synthesis of the lithium salt N, N'-bis(benzene sulfonyl) amide pentane iminosulfinic acid.

A 0.01 mole (4.14 g) solution of pentane iminosulfinic acid N, N'-bis(benzene sulfonyl)amide was prepared in 50 ml of acetone. An equivalent amount of lithium hydroxide (0.01 mole) in methanol was added. The reactant mixture was stirred for 30 minutes at a temperature of 18–20° C. After evaporation of the solvents in the open air, the residue was dried for 7 days in an exicator above $CaCl_2$ (nonaqueous). 4.18 g (0.00995 mole) of the lithium salt N,N'-bis(benzene sulfonyl)amide pentane iminosulfinic acid was produced, resulting in a yield of about 99.5%. This product forms hygroscopic white crystals with a melting point 89° C. (with partial decomposition). The experimentally found content of N was 6.59 wt %. The theoretical N wt % for $C_{17}H_{21}N_2O_4S_3$ is 6.6%).

IR (neat; KBr plates): $SO_2$ (s) 1160 $cm^{-1}$, $SO_2$ (as) 1330 $cm^{-1}$,

S=N 1040 $cm^{-1}$.

EXAMPLE 2
Synthesis N, N'-bis(para-toluene sulfonyl)amide pentane iminosulfinic acid.

A 0.01 mole (4.42 g) solution of the lithium salt bis (para-toluene sulfonyl)amide pentane iminosulfinic acid was prepared in acetone (80 ml). An equivalent amount of lithium hydroxide was added. The reactant mixture was stirred for 20 minutes at a temperature of 8–20° C. The solvents were evaporated in the open air and the residue was dried for 7 days in an exicator over $CaCl_2$ (nonaqueous). 4.44 g (0.0099 mole) of the lithium salt of N, N'-bis(p-toluene sulfonyl)amide pentane iminosulfinic acid was produced yielding about 99.2%. This compound forms hydroscopic crystals with a melting point 148° C. (being decomposed).

The experimental content of N in the product was determined to be 6.18% compared to a theoretical wt % N for $C_{19}H_{26}N_2O_4S_3$ being 6.25%.

IR (neat; KBr plates): $SO_2$ (S) 1165 $cm^{-1}$, $SO_2$ (as) 1330 $cm^{-1}$, S=N 1030 $cm^{-1}$.

EXAMPLE 3
Electrical Performance of a Non-Aqueous Electrolyte Using one of the Organic Salts The lithium salt N, N'-bis(para-toluene sulfonyl)amide pentane iminosulfinic acid formed by the method of Example 2 was dissolved in dimethyl formamide at room temperature.

The electrical conductivity of this electrolyte was measured using an AC bridge of the type R-5021 by assuming the various impedance components were series connected. From the frequency dependence of the impedance, a working frequency of f=80 kHz was selected. An experimental glass electrochemical cell with parallel flat Pt electrodes was held in a thermostat. The specific conductivity was determined as $\chi=K \cdot G$, where $\chi$ (Sm/cm) is the specific conductivity of the electrolyte, G (Sm) is the conductivity of the electrolyte in the cell, and K ($cm^{-1}$) is the cell's constant which was determined by using a standard 0.01 M KCl solution. The conductivity of 0.24M $C_5H_{11}(NSO_2C_6H_5)$ $SNLiSO_2C_6H_5$ in DMFA was measured to be $6.0 \times 10^{-3}$ Sm/cm.

EXAMPLE 4
Conductivity of a Liquid Electrolyte Including an Organic Salt

The Lithium salt of N,N'-bis(p-toluenesulfonyle)amide of pentaneiminosulfinic acid was dissolved in propylene carbonate at room temperature. The ionic conductivity of 0.5M $C_5H_{11}S(=NSO_2C_6H_5)NLiSO_2C_6H_5$ in a propylene carbonate solvent was measured to be $5.2 \times 10^{-4}$ Sm/cm.

EXAMPLE 5
Cycling Stability

Figure 1:
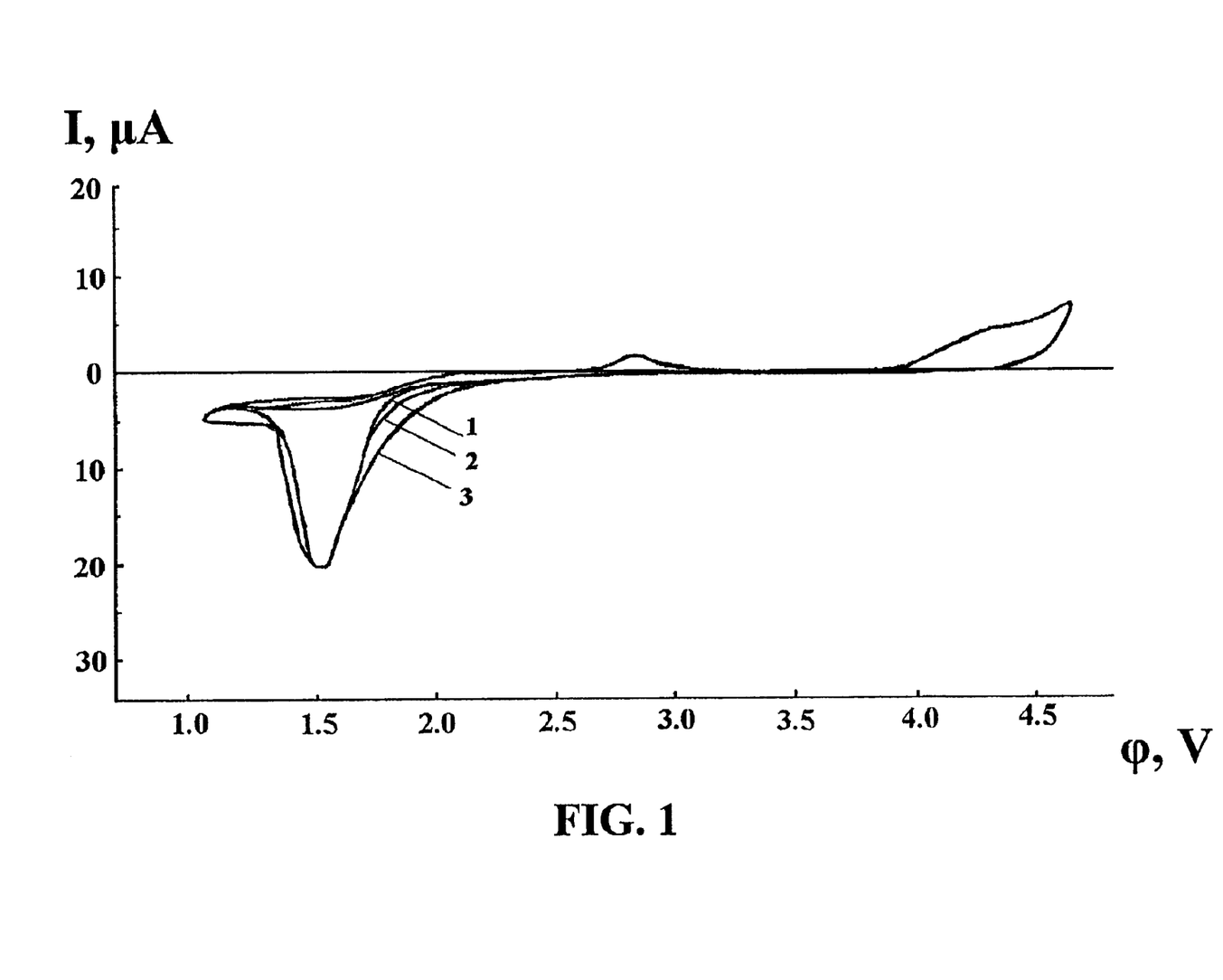
FIG. 1 is data showing the cycling stability of a liquid electrolyte based electrochemical cell, the electrolyte including a 0.5M solution of $C_5H_{11}S(=NSO_2C_6H_5)NLiSO_2C_6H_5$ in a propylene carbonate solvent.

Cycling stability of a cell including a liquid electrolyte comprising a 0.5M solution of $C_5H_{11}(NSO_2C_6H_5)$ $NLiSO_2C_6H_5$ in a propylene carbonate solvent was investigated using potentiodynamic cycling. The experiment was carried out in three-electrode cell of coin-type construction manufactured of polytetrafluoroethylene and consisting of working electrode, reference electrode and an auxiliary electrode in an argon atmosphere. The reference electrodes and auxiliary electrode were made of lithium. For the investigation of the background potentiodynamic characteristics of the electrolyte, a platinum plate served as a working electrode. The working electrode areas were $8.0 \times 10^{-3}$ $cm^2$.

Electrode potential sweep was performed from a potentiostat model PI-50-1.1 (Measuring Instrument Plant, Gomel', Byelorussia) and programmer model PR-8 (Measuring Instrument Plant, Gomel', Byelorussia). The scan rate used ranged from $1 \times 10^{-3}$ to $1 \times 10^{-4}$ V/s. The curves were registered on a two-coordinate PDA-1 recorder (Measuring Instrument Plant, Krasnodar, Russia) within a potential range 1.1–4.6 V with platinum electrodes. Labels on curves correspond to the number of cycles.

FIG. 1 demonstrates that the liquid electrolyte comprising $C_5H_{11}(NSO_2C_6H_5)NLiSO_2C_6H_5$ in propylene carbonate was found to be quite stable over a wide voltage range.

EXAMPLE 6
Electrolyte Conductivity

A mixture of $VF_2$/HFP copolymer (20810 from Solvay/Belgium) (29.7 wt %), PC (59.9 wt %), and $C_5H_{11}S$($=NSO_2C_6H_5$)$NLiSO_2C_6H_5$ (10.4 wt %) were dissolved in 10 ml of acetone. A homogenous solution was formed and casted upon a glass support. The film was dried for 12 hours at room temperature and 24 hours at 45° C. under vacuum. Impedance measurements in a Ni/PE/Ni system produced a measured polymer electrolyte film conductivity of approximately $4.5 \times 10^{-6}$ Sm/cm.

EXAMPLE 7
Electrolyte Conductivity

A mixture of $VF_2$/HFP copolymer (20810 from Solvay/Belgium) (18.1 wt %), PC (72.5 wt %), $LiClO_4$ (3.1 wt %) and $C_5H_{11}S(=NSO_2C_6H_5)NLiSO_2C_6H_5$ (6.3 wt %) were dissolved in 10 ml acetone. A homogenous solution formed was casted upon a glass support. The film was dried for 12 hours at room temperature and 24 hours at 45° C. under vacuum. Impedance measurements in a Ni/PE/Ni system produced a measured polymer electrolyte film conductivity of approximately $8.4 \times 10^{-4}$ Sm/cm.

EXAMPLE 8
Electrolyte Conductivity

A mixture of chlorinated PVC (18.1 wt %), the chlorine content of chlorinated PVC being approximately 61.4%, PC (72.5 wt %), $LiClO_4$(3.1 wt %) and $C_5H_{11}S(=NSO_2C_6H_5)NLiSO_2C_6H_5$ (6.3 wt %) were dissolved in 10 ml acetone. A homogenous solution was formed and was casted upon a glass support. The film was dried for 12 hours at room temperature and 24 hours at 45° C. under vacuum. Impedance measurements in a Ni/PE/Ni system produced measured polymer electrolyte film conductivity of approximately $5.24 \times 10^{-4}$ Sm/cm.

EXAMPLE 9
Electrolyte Conductivity

A mixture of $VF_2$/HFP copolymer (20810 from Solvay/Belgium/) (18.1 wt %), PC (72.5 wt %) $LiCF_3SO_3$(3.1 wt %) and $C_5H_{11}S(=NSO_2C_6H_5)NLiSO_2C_6H_5$ (6.3 wt %) were dissolved in 10 ml acetone. A homogenous solution was formed and was casted upon a glass support. The film was dried for 12 hours at room temperature and 24 hours at 45° C. under vacuum. Impedance measurements in a Ni/PE/Ni system produced measured polymer electrolyte film conductivity of approximately $2.95 \times 10^{-4}$ Sm/cm.

EXAMPLE 10
Electrolyte Conductivity

A mixture of chlorinated PVC (18.1 wt %), the chlorine content of chlorinated PVC being approximately 61.4%, PC (72.5 wt %), $LiCF_3SO_3$ (3.1 wt %) and $C_5H_{11}S(=NSO_2C_6H_5)NLiSO_2C_6H_5$ (6.3 wt %) were dissolved in 10 ml acetone. A homogenous solution was formed and was casted upon a glass support. The film was dried for 12 hours at room temperature and 24 hours at 45° C. under vacuum. Impedance measurements in a Ni/PE/Ni system produced a measured polymer electrolyte film conductivity of approximately $1.25 \times 10^{-4}$ Sm/cm.

EXAMPLE 11
Cycling Stability

Figure 2:
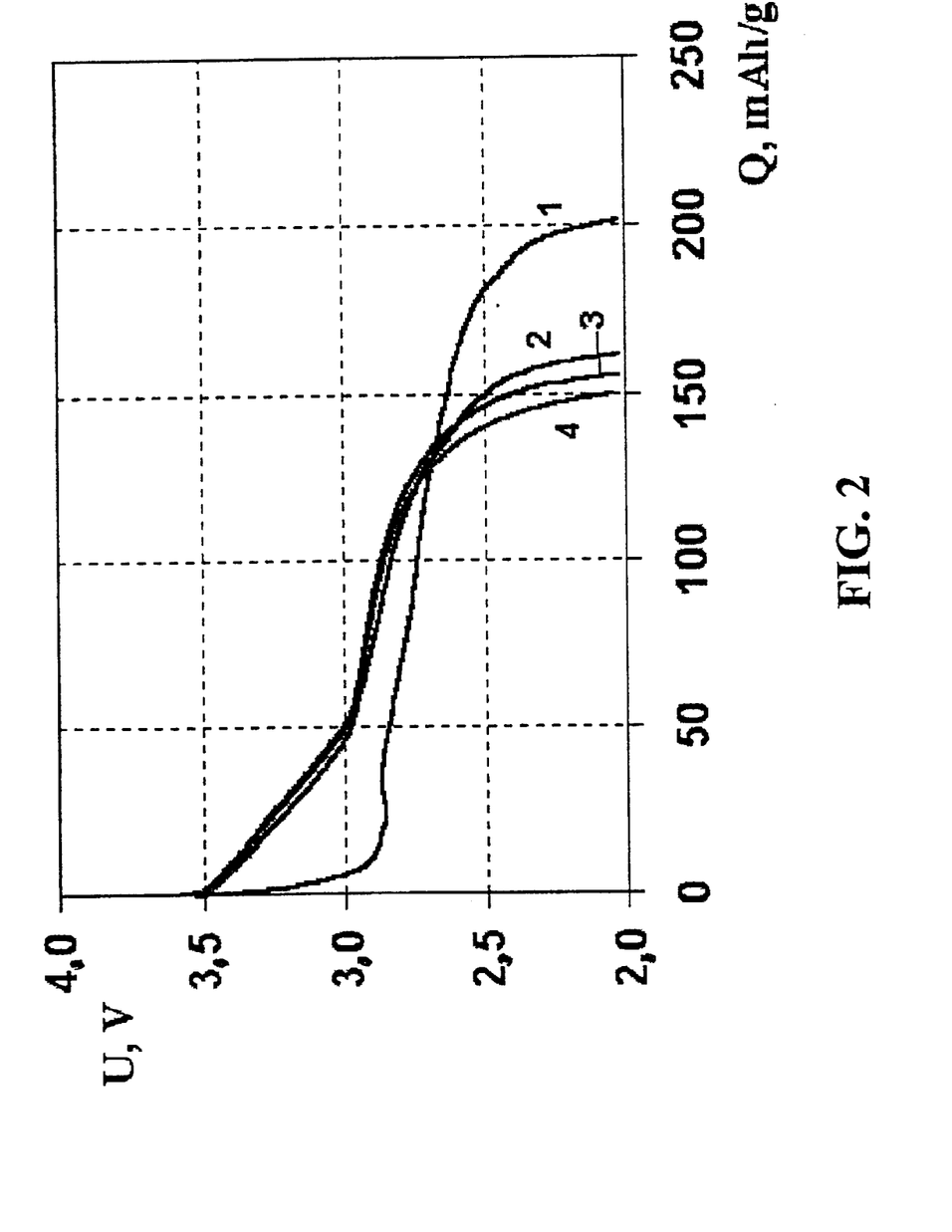
FIG. 2 is data showing the change in discharge capacity during cycling of a Li—$MnO_2$ system having a polymer electrolyte including C—PVC:PC:$LiClO_4$: $C_5H_{11}S$ (=$NSO_2C_6H_5$)$NLiSO_2C_6H_5$ (18.1:72.5:3.1:6.3 wt %).

An experiment was performed to determine the change in discharge capacity during long-time cycling of a rechargeable Li—$MnO_2$ system having a modified polymer electrolyte. The electrolyte composition was C—PVC:PC:$LiClO_4$:$C_5H_{11}S(=NSO_2C_6H_5)NLiSO_2C_6H_5$ (18.1:72.5:3.1:6.3 wt %). Results are shown in FIG. 2. Numbers correspond to the number of cycles.

The rechargeable Li/PE/$MnO_2$ battery having the size of a 2325 coin cell was prepared by interposing layers of the polymer electrolyte (prepared according to Example 8 and with a thickness of 0.08 mm) between a metallic lithium anode (thickness 0.8 mm), and a cathode prepared from a mixture of $MnO_2$ (80 wt %), carbon black (5 wt %), graphite (5 wt %) and a binder, using a suspension of the fluorinated polymer polytetrafluoroethylene (10 wt %). Before assembly, the cathode mass was annealed for 3 hours at 250° C.

The battery formed was cycled at 20° C. between 2.0 and 3.7 V with a current 0.1 mA during discharge and 0.1 mA during charging. The results shown in FIG. 2 indicate a high level of cycling stability.

EXAMPLE 12
Cycling Stability

Figure 3:
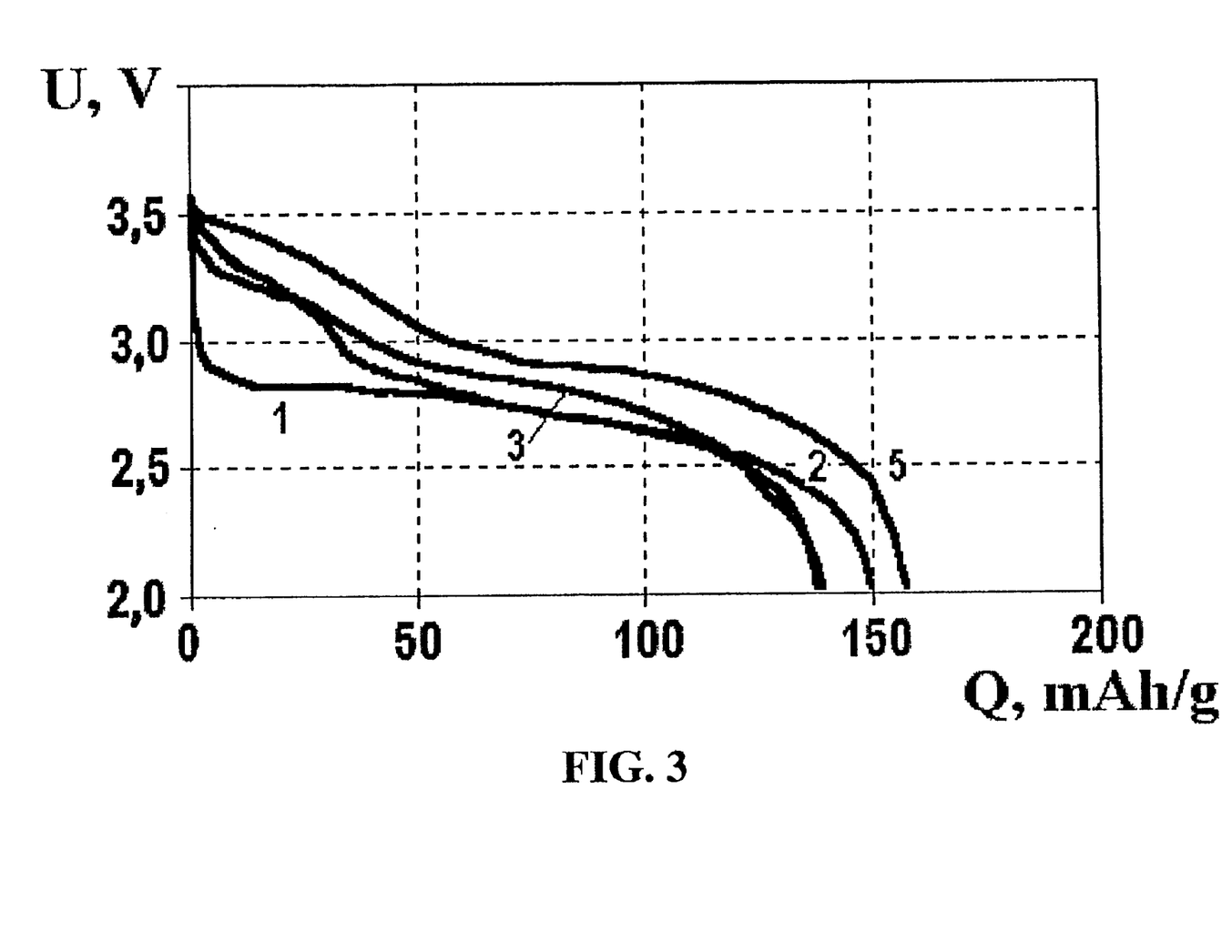
FIG. 3 is data showing the change in discharge capacity during cycling of a Li—$MnO_2$ system having a polymer electrolyte including C—PVC:PC:$LiClO_4$ (19.2:75.8:5.0 wt %).

An experiment was performed to determine the change in discharge capacity during long-time cycling of a rechargeable Li—$MnO_2$ system having a non-modified polymer electrolyte. The electrolyte composition was C—PVC:PC:$LiClO_4$ (19.2:75.8:5.0 wt %). Results are shown in FIG. 3. Numbers correspond to the number of cycles.

The rechargeable battery Li/PE/$MnO_2$ battery had the size of a 2325 coin cell and was prepared by interposing layers of the polymer electrolyte (thickness of 0.08 mm) between a metallic lithium anode (thickness of 0.8 mm), and a cathode. The polymer electrolyte was prepared according to the following method. A mixture of chlorinated PVC (19.2 wt %), the chlorine content of chlorinated PVC being approximately 61.4%, PC (75.8 wt %) and $LiClO_4$(5.0 wt %) were dissolved in 10 ml acetone. A homogenous solution formed was casted upon a glass support. The film was dried for 12 hours at room temperature and 24 hours at 45° C. under vacuum.

The cathode was prepared from a mixture of $MnO_2$ (80 wt %), carbon black (5 wt %), graphite (5 wt %) and a binder, using a suspension of the fluorinated polymer polytetrafluoroethylene (10 wt %). The cathode mass was annealed for 3 hours at 250° C. before assembly.

The battery was cycled at 20° C. between 2.0 and 3.7 V with a current 0.1 mA during discharge and 0.1 mA during charging (FIG. 3).

The results shown in FIGS. 2 and 3 indicate that discharge capacity at the first cycle of the Li—$MnO_2$ system based on non-modified polymer electrolyte is lower, than in the case of the polymer electrolyte modified by $C_5H_{11}S(=NSO_2C_6H_5)NLiSO_2C_6H_5$. Besides, in the case of application of modified polymer electrolytes the values of discharge capacity during cycling are more stable.

EXAMPLE 13
Cycling Stability

Figure 4:
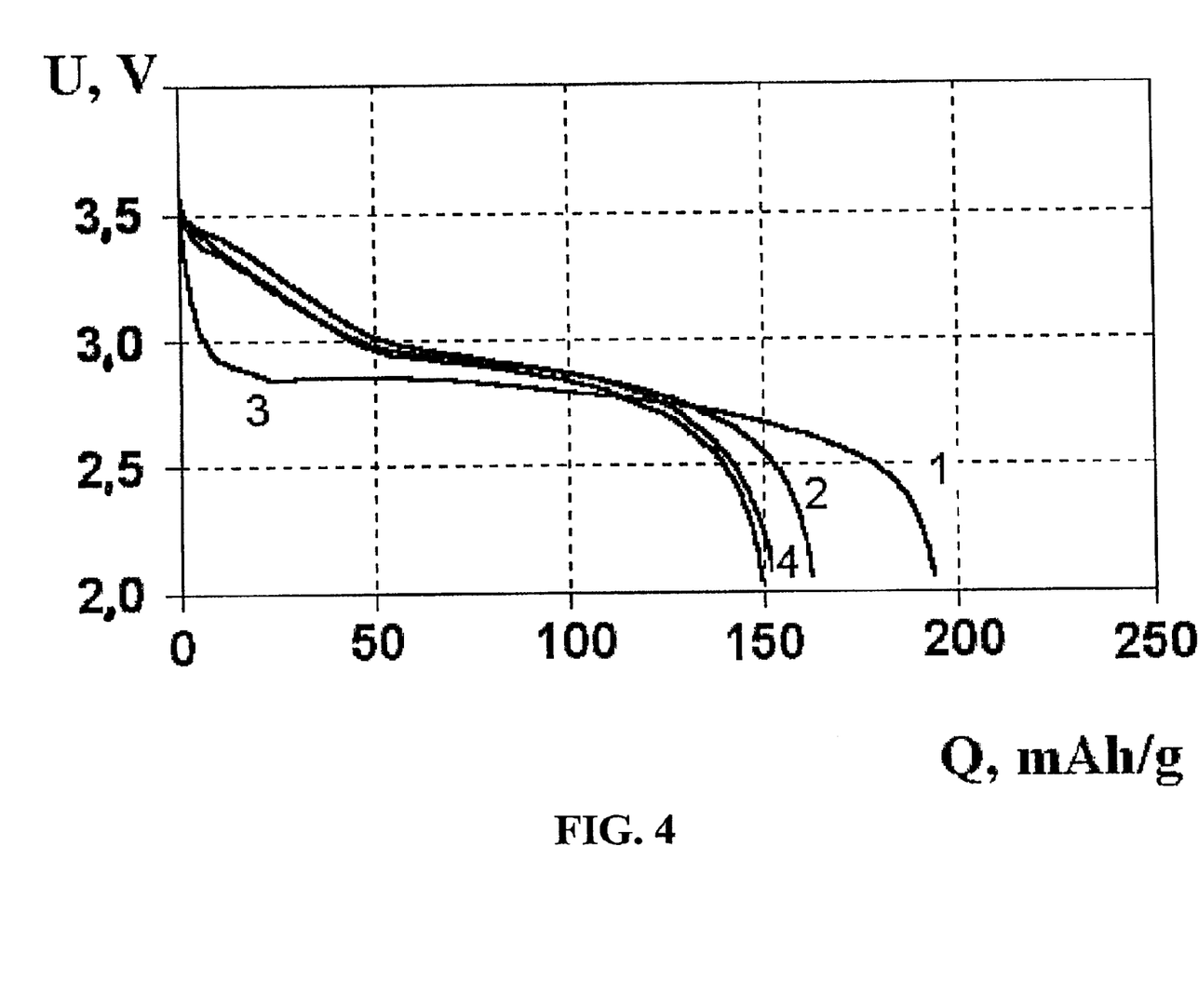
FIG. 4 is data showing the change in discharge capacity during cycling of a Li—$MnO_2$ system having a polymer electrolyte including C—PVC:PC:$LiCF_3SO_3$: $C_5H_{11}S$ (=$NSO_2C_6H_5$)$NLiSO_2C_6H_5$ (18.1:72.5:3.1:6.3 wt %).

An experiment was performed to determine the change in discharge capacity during long-time cycling of a rechargeable Li—$MnO_2$ system having a modified polymer electrolyte. The electrolyte composition was C—PVC:PC:$LiCF_3SO_3$:$C_5H_{11}S(=NSO_2C_6H_5)NLiSO_2C_6H_5$ (18.1:72.5:3.1:6.3 wt %). Results are shown in FIG. 4. Numbers correspond to the number of cycles.

The rechargeable battery Li/PE/$MnO_2$ battery having the size of a 2325 coin cell was prepared by interposing layers of the polymer electrolyte (prepared according to Example 10 and with a thickness of 0.03 mm) between a metallic lithium anode (thickness of 0.8 mm), and a cathode prepared from a mixture of $MnO_2$ (80 wt %), carbon black (5 wt %), graphite (5 wt %) and a binder, using a suspension of the fluorinated polymer polytetrafluoroethylene (10 wt %). The cathode mass was annealed for 3 hours at 250° C. before assembly.

The battery was cycled at 20° C. between 2.0 and 3.7 V with a current 0.1 mA during discharge and 0.1 mA during charging. The results shown in FIG. 4 indicate a high level of cycling stability.

EXAMPLE 14

Cycling Stability

Figure 5:
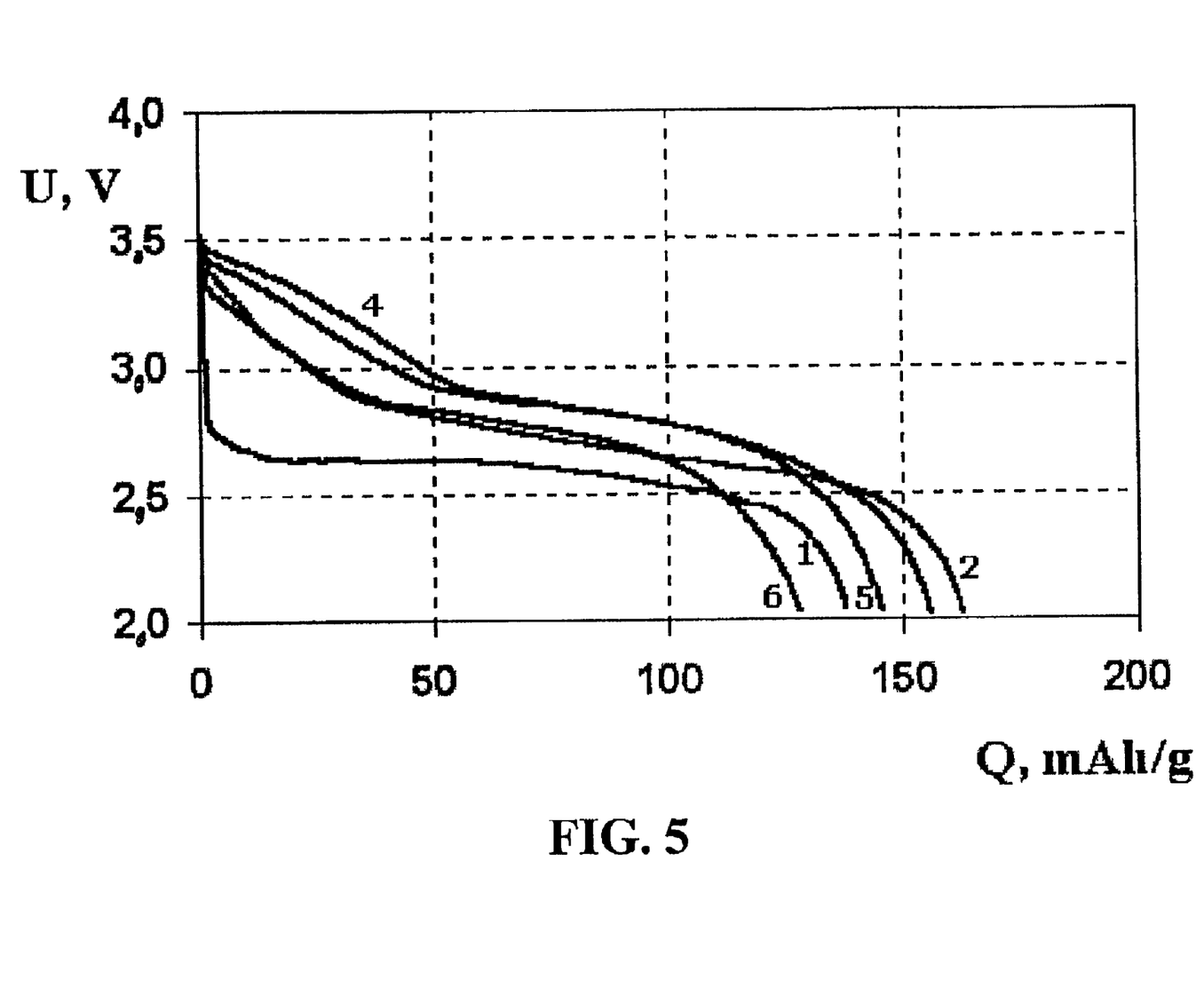
FIG. 5 is data showing the change in discharge capacity during cycling of a Li—$MnO_2$ system having a polymer electrolyte including C—PVC:PC:$LiCF_3SO_3$ (19.2:75.1:5.7 wt %).

An experiment was performed to determine the change in discharge capacity during long-time cycling of a rechargeable Li—$MnO_2$ system having a non-modified polymer electrolyte. The electrolyte composition was C—PVC:PC:$LiCF_3SO_3$ (19.2:75.1:5.7 wt %). Results are shown in FIG. 5. Numbers correspond to the number of cycles.

The rechargeable battery Li/PE/$MnO_2$ battery having the size of a 2325 coin cell was prepared by interposing layers of the polymer electrolyte (thickness of 0.03 mm) between a metallic lithium anode (thickness of 0.8 mm), and a cathode prepared from a mixture of $MnO_2$ (80 wt %), carbon black (5 wt %) graphite (5 wt %) and a binder, using a suspension of the fluorinated polymer polytetrafluoroethylene (10 wt %).

The polymer electrolyte was prepared as follows. A mixture of chlorinated PVC (19.2 wt %), the chlorine content of chlorinated PVC being approximately 61.4%, PC (75.1 wt %) and $LiCF_3SO_3$(5.7 wt %) were dissolved in 10 ml acetone. A homogenous solution formed was casted upon a glass support. The film was dried for 12 hours at room temperature and 24 hours at 45° C. under vacuum. The cathode mass was annealed for 3 hours at 250° C. before assembly. The battery was cycled at 20° C. between 2.0 and 3.7 V with a current 0.1 mA during discharge and 0.1 mA during charging (FIG. 5).

The results shown in FIGS. 4 and 5 indicate that discharge capacity at the first cycle of the Li—$MnO_2$ system based on non-modified polymer electrolyte is lower, than in the case of the polymer electrolyte modified by $C_5H_{11}S$ (=$NSO_2C_6H_5$)$NLiSO_2C_6H_5$. Besides, in the case of application of modified polymer electrolytes the values of discharge capacity during cycling are more stable.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

We claim:

1. A non-aqueous electrolyte, comprising:

an aprotic solvent, and an organic salt, said organic salt being an alkali metal bound to a disubstituted amide of alkane sulfinic acid, wherein a tetravalent sulfur atom in said salt is directly bonded to said alkane.

2. The electrolyte of claim 1, wherein said organic salt has the following general formula:

where Ar is an aromatic, M is at least one selected from the group consisting of Li, K and Na, and $C_xH_y$ comprises an alkane selected from the group consisting of methane, ethane, propane, butane, pentane, hexane, heptane, octane and nonane.

3. The electrolyte of claim 1, wherein said alkali metal is at least one selected from the group consisting of Li, K and Na.

4. The electrolyte of claim 2, wherein said alkane is selected from the group consisting of methane, ethane, propane, butane, pentane, hexane, heptane, octane and nonane.

5. The electrolyte of claim 1, wherein said amides are at least one selected from the group consisting of benzene sulfonyl amide and para-toluene sulfonyl amide.

6. The electrolyte of claim 1, wherein said amides are both benzene sulfonyl amide.

7. The electrolyte of claim 1, wherein said amides are both para-toluene sulfonyl amide.

8. The electrolyte of claim 1, wherein said aprotic solvent comprises at least one selected from the group consisting of acrylonitrile, dimethyl formamide, dimethyl acetamide, dimethyl sulfoxide, propylene carbonate, ethylene carbonate, dimethyl carbonate, gamma-butyrolactone, 1,3-dioxolane, diglyme, dimethoxy ethane and sulfolane, and mixtures thereof.

9. The electrolyte of claim 1, wherein up to 20 weight percent of said electrolyte is said organic salt.

10. The electrolyte of claim 1, further comprising at least one inorganic salt, said inorganic salt being at least one selected from the group consisting of $LiClO_4$, $LiBF_4$, $LiAsF_6$, $LiCF_3SO_3$ and $LiN(CF_3SO_2)_2$.

11. The electrolyte of claim 1, wherein up to 10 weight percent of said electrolyte is said inorganic salt.

12. The electrolyte of claim 1, further comprising a polymer material, wherein said liquid electrolyte is integrated with said polymer material to form a gel or plasticized polymer electrolyte.

13. The electrolyte of claim 12, wherein said polymer material is at least one selected from the group consisting of polyethylene oxide, polyacrylonitrile, polymethylmethacrylate, a halogen-containing polymer, and their copolymers.

14. The electrolyte of claim 13, wherein said halogen-containing polymer is at least one selected from the group consisting of polyvinyl chloride, chlorinated polyvinyl chloride, polyvinylidene fluoride, and their copolymers.

15. The electrolyte of claim 12, wherein said polymeric material is 10 to 85 weight percent of said electrolyte.

16. The electrolyte of claim 12, wherein 10 to 82 weight percent of said electrolyte is said aprotic solvent.

17. A method for forming an alkali disubstituted amide of an alkane iminosulfinic acid salt, comprising the steps of:

providing disubstituted amides of alkane iminosulfinic acid, a source of alkali metal ions and at least one organic solvent, and mixing said substituted alkane iminosulfinic acid with said source alkali of metal ions and said organic solvent.

18. The method of claim 17, further comprising the step of evaporating said organic solvent.

19. The method of claim 17, wherein said source of alkali metal ions comprises at least one alkali metal hydroxide or at least one alkali metal alcoholate.

20. The method of claim 17, wherein said amides are at least one selected from the group consisting of benzene sulfonyl amide and para-toluene sulfonyl amide.

21. A method of forming a liquid electrolyte, comprising the steps of:
providing an aprotic solvent, an inorganic salt of an alkali metal and an organic salt, said organic salt being an alkali metal bound to a disubstituted amide of alkane sulfinic acid; and
mixing together said aprotic solvent, said inorganic salt and said organic salt.

22. A method of forming a polymer electrolyte, comprising the steps of:
providing an aprotic solvent, a inorganic salt of an alkali metal, a polymer, and an organic salt, said organic salt being an alkali metal bound to a disubstituted amide of alkane sulfinic acid, and
mixing together said aprotic solvent, said inorganic salt, said polymer and said organic salt.

23. The method of claim 22, wherein said polymer comprises chlorinated PVC or PVDF.

24. An electrochemical cell, comprising:
a lithium metal or lithium ion containing anode;
a cathode, and
an electrolyte operatively associated with said anode and cathode, said electrolyte selected from the electrolyte of claim 1 or the electrolyte of claim 12.

25. The electrochemical cell of claim 24, wherein said battery is rechargeable.

26. The electrochemical cell of claim 24, wherein said anode comprises a lithium alloy.

27. The electrochemical cell of claim 26, wherein said lithium alloy is at least one selected from the group consisting of lithium-aluminum, lithium-aluminum-silicon, lithium-aluminum-cadmium, lithium-aluminum-bismuth and lithium-aluminum-tin.

28. The electrochemical cell of claim 24, wherein said anode comprises said lithium ions, said anode including graphite.

29. The electrochemical cell of claim 24 wherein said cathode comprises a metal oxide.

30. The electrochemical cell of claim 29, wherein said metal oxide is a lithium-transition metal oxide.

31. The electrochemical cell of claim 30, wherein said metal oxide is at least one selected from the group consisting of $MnO_2$, $LiMn_2O_4$, $V_2O_5$ and $V_6O_{13}$.

32. A method of forming an electrochemical cell, comprising the steps of:
providing an anode comprising an alkali metal or an alkali ion, a cathode, and a non aqueous electrolyte including an organic salt, said organic salt being an alkali metal bound to a disubstituted amide of alkane sulfinic acid, and
operatively associating an electrolyte with said anode and cathode.

* * * * *